United States Patent
Ito et al.

[11] Patent Number: 5,480,775
[45] Date of Patent: Jan. 2, 1996

[54] METHOD FOR MEASURING A SPECIMEN BY THE USE OF FLUORESCENT LIGHT

[75] Inventors: Yuji Ito, Chigasaki; Atsushi Saito, Yokohama, both of Japan

[73] Assignee: Canon Kabushiki Kaisha, Tokyo, Japan

[21] Appl. No.: 55,759

[22] Filed: May 3, 1993

Related U.S. Application Data

[63] Continuation of Ser. No. 644,328, Jan. 22, 1991, abandoned.

[30] Foreign Application Priority Data

Jan. 26, 1990 [JP] Japan ................................. 2-16551
Jan. 26, 1990 [JP] Japan ................................. 2-16552

[51] Int. Cl.⁶ .................................................. G01N 33/554
[52] U.S. Cl. .......................... 435/7.2; 356/317; 356/318; 356/337; 356/338; 435/7.21; 435/808; 435/968; 436/164; 436/172; 436/525; 436/528; 436/531; 436/533; 436/537; 436/538; 436/548; 436/800; 436/805
[58] Field of Search ........................... 356/317, 318, 356/337, 338; 436/164, 172, 523, 528, 531, 533, 525, 538, 537, 800, 805, 548; 435/808, 968, 7.2, 7.21

[56] References Cited

U.S. PATENT DOCUMENTS

| | | | |
|---|---|---|---|
| 4,006,360 | 2/1977 | Mueller | 250/461 |
| 4,243,318 | 1/1981 | Stör | 356/39 |
| 4,341,957 | 7/1982 | Wieder | 250/461.2 |
| 4,374,120 | 2/1983 | Soini et al. | 436/800 |
| 4,573,796 | 3/1986 | Martin et al. | 356/318 |
| 4,582,809 | 4/1986 | Block et al. | 436/527 |
| 4,587,223 | 5/1986 | Soini et al. | 436/172 |
| 4,668,868 | 5/1987 | Noller | 250/458.1 |
| 4,690,561 | 9/1987 | Ito | 356/339 |
| 4,715,708 | 12/1987 | Ito | 356/72 |
| 4,822,733 | 4/1989 | Morrison | 436/805 |
| 4,918,000 | 4/1990 | Schubert | 436/548 |
| 4,999,513 | 3/1991 | Ito et al. | 250/575 |
| 5,047,321 | 9/1991 | Loken et al. | 436/548 |

FOREIGN PATENT DOCUMENTS

| | | |
|---|---|---|
| 0177813 | 4/1986 | European Pat. Off. |
| 2628158 | 2/1977 | Germany |
| 60-188845 | 9/1985 | Japan |
| 2172104 | 12/1985 | United Kingdom |

*Primary Examiner*—David Saunders
*Assistant Examiner*—Christopher L. Chin
*Attorney, Agent, or Firm*—Fitzpatrick, Cella, Harper & Scinto

[57] ABSTRACT

A method of and an apparatus for measuring a specimen by the use of fluorescence light which has the step of dyeing the specimen with a fluorescence dye, the step of applying light to the dyed specimen and exciting the fluorescence dye, and the step of detecting fluorescence light from the excited specimen within a period which does not substantially overlap with the period of the application, and which can accurately detect the excited desired fluorescence light.

14 Claims, 4 Drawing Sheets

5,480,775

METHOD FOR MEASURING A SPECIMEN BY THE USE OF FLUORESCENT LIGHT

This application is a continuation of application Ser. No. 07/644,328 filed Jan. 22, 1991, now abandoned.

BACKGROUND OF THE INVENTION

Field of the Invention

This invention relates to a method and an apparatus wherein light is applied to individual specimens and scattered lights and fluorescence light created thereby are optically detected to thereby accomplish measurement of the specimens.

Related Background Art

A flow cytometer is known as an example of the prior-art specimen examining apparatus. Specimens in blood corpuscle cells or the like in sample liquid are fluorescence-dyed and these specimens are caused to flow one by one to an examined portion to which a light beam is applied and as a result, scattered lights, fluorescence light, etc. created from the individual specimens passing through the examined portion are wavelength-sorted and metered, whereby the analysis of the specimens is effected from the statistical tendency of measurement parameters regarding a number of specimens. Thereby, the DNA analysis of cells, the search of surface antigen, etc. become possible.

Generally, however, when light is applied to fluorescence-dyed specimens, not only do desired fluorescence light created by fluorescence dye become excited, but also self-fluorescence light possessed by the specimens themselves and further, self-fluorescence light possessed by suspended matters such as dust and fluid itself are created at the same time. Such fluorescence light is created over a wide wavelength range and therefore, self-fluorescence light in the same wavelength range as the desired fluorescence light emitted from the fluorescence dye cannot be optically wavelength-sorted. Thus, the intensity of fluorescence light consisting of the desired fluorescence light and the self-fluorescence light mixed as miscellaneous light therewith is metered.

Also, where there is not a laser source of a single wavelength, but a multi-oscillation laser source, a white light source or the like is used as a light source, there is the undesirable possibility that scattered light of the same wavelength range as desired fluorescence light included in the illuminating light from these light sources is mixed as miscellaneous light with the metered value of the desired fluorescence light.

That is, in the prior-art apparatus, there has been the possibility that miscellaneous light is included as an error in the metered intensity of fluorescence light and the S/N ratio of the resultant measured value of the fluorescence light becomes worse.

SUMMARY OF THE INVENTION

It is an object of the present invention to provide a method and an apparatus which can detect the intensity of genuinely desired fluorescence light without being affected by miscellaneous light.

It is a further object of the present invention to obtain different fluorescence light parameters equal to or greater than the number of photodetectors in the above-described method and apparatus.

It is still a further object of the present invention to provide a reagent for use in the above-described method and apparatus, and a method of making said reagent.

DESCRIPTION OF THE PREFERRED EMBODIMENTS

Figure 1:
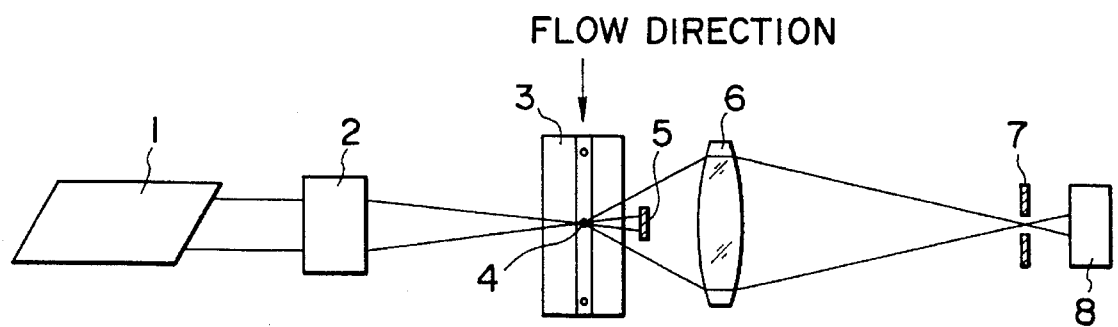
FIGS. 1 and 2 show the construction of an apparatus according to a first embodiment of the present invention.

Some embodiments of the present invention will hereinafter be described in detail with reference to the drawings. FIG. 1 shows an optical arrangement when the apparatus of an embodiment is seen from a side thereof, and FIG. 2 shows the optical arrangement when the apparatus is seen from above it.

Sample liquid such as a blood sample or carrier particle suspended liquid in which minute specimens are suspended is prepared, and this sample liquid is dye-treated as a pre-treatment by a fluorescent reagent and regulated into an appropriate reaction time and concentration. On the other hand, sheath liquid such as physiological saline solution or distilled water is prepared. Then, these liquids are pressurized by a pressurizing mechanism, not shown, and are directed to a flow cell 3, and a fine stream of sample liquid is formed in such a manner as to wrap the sample liquid in the sheath liquid by the sheath flow principle. At this time, specimens contained in the sample liquid, i.e., minute particles such as individual cells and latices are separated from one another and successively flow one by one from above to below as viewed in the plane of the drawing sheet. Laser light emitted from a laser source 1 (in the present embodiment, ultraviolet laser of wavelength 300 nm) is applied to the flow of these particles while being converged into any elliptical shape by an imaging optical system 2 having two cylindrical lenses whose bus bar directions are a flow-through portion direction and orthogonal to the flow-through portion direction, respectively. Preferably, the shape of the light beam applied to the particles may generally be an elliptical shape having its major diameter in a direction orthogonal to the flow. This is for the purpose of causing the light beam to be applied to the particles with uniform intensity even if the position of the flow of the individual particles somewhat fluctuates in the fluid.

When the light beam is applied to the particles, there are created scattered lights and fluorescence light. Of the thus created scattered lights, the forwardly scattered light created in the forward direction is metered by a condensing lens 6, an aperture 7 and a photodetector 8. The opening portion of the aperture 7 is disposed conjugately with a light applying position 4 so that only the light from the light applying position 4 may be directed to the photodetector 8. In order to prevent the applied powerful light beam from directly entering the photodetector 8, a minute stopper 5 of light absorbing property is disposed short of the condensing lens 6 in the optical path, whereby there is constructed a dark field optical system so that the direct light from the light source and light transmitted through the particles may be removed. Thereby, only the light scattered from the light applying position 4 can be metered. Thus, in this construction, the intensity of light including the fluorescence light as well as the forwardly scattered light is metered, but there is no problem because the intensity of the fluorescence light is generally very weak as compared with the intensity of the forwardly scattered light. Of course, a band-pass filter for selectively transmitting the scattered light wavelengths therethrough may be disposed short of the photodetector 8.

Figure 2:
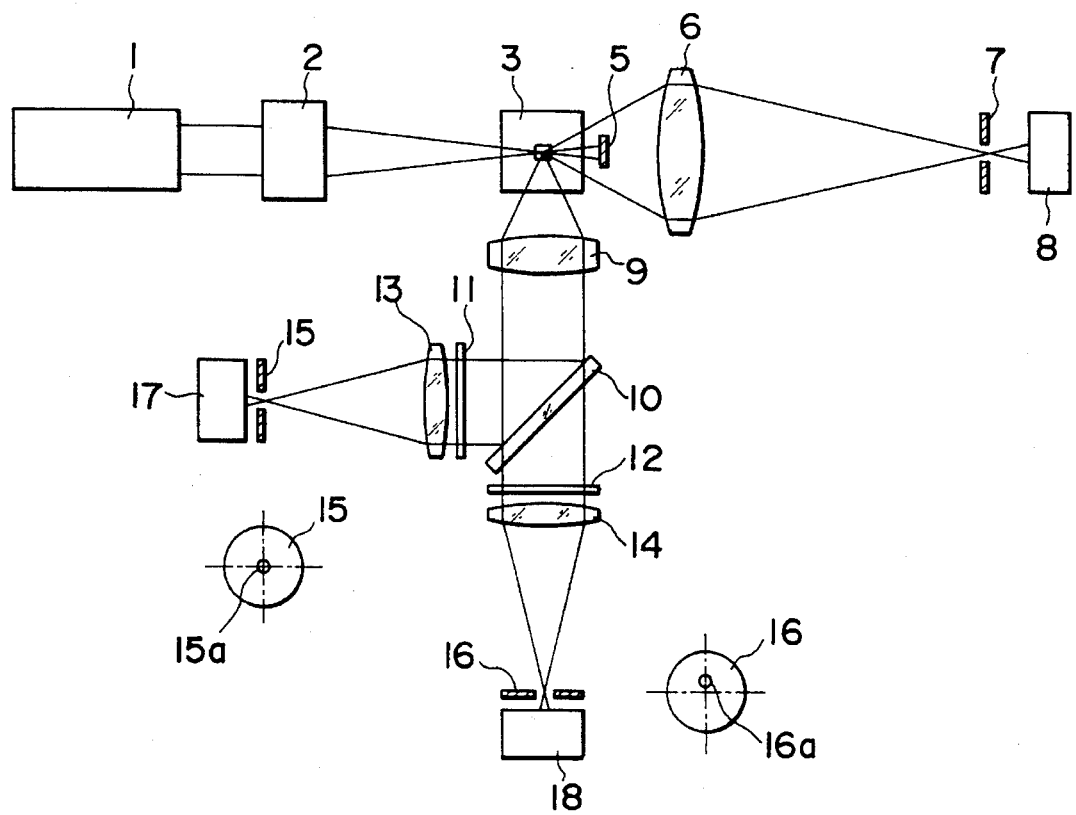

Of the scattered lights, the light created in a sideways direction orthogonal to the optic axis of the laser and to the flow of the particles is condensed by the condensing lens 9 as shown in FIG. 2. The condensed light has its wavelength component of the set wavelength or below reflected by a dichroic mirror 10, and via a band-pass filter 11 for selectively transmitting the wavelengths of the scattered lights, i.e., the wavelength of the laser light (in the vicinity of 300 nm) therethrough, a condensing lens 13 and an aperture 15, the sideways scattered light is metered by a photodetector 17. The aperature 15 has its opening portion 15a provided at the center of the optic axis as shown, and the opening portion 15a is in conjugate relationship with the light applying position 4 so that only the scattered light created from the light applying position 4 may be detected by the photodetector 17.

Also, in order that fluorescence light of long fluorescence life created from the particles may be metered during a non-application period, the fluorescence light condensed by the condensing lens 9 and passed through the dichroic mirror 10 is wavelength-selected by a band-pass filter 12 for fluorescence wavelength, and fluorescence light of a particular wavelength is detected by the set of a condensing lens 14, an aperture 16 and a photodetector 18. The aperture 16 has its opening portion 16a provided somewhat above the center thereof, as shown. That is, the opening portion 16a is conjugate with a position somewhat downstream of the light applying position so as to direct only the fluorescence light of the particular wavelength from a non-applying position downstream of the light applying position 4 to the photodetector 18. That is, the light does not enter the photodetector 17 for metering the scattered light and the photodetector 18 for metering the fluorescence light, at a time, and the scattered light is detected during an application period and the fluorescence light is detected during the non-application period so that the output pulse of each photodetector may be time-serially obtained.

Figure 3:
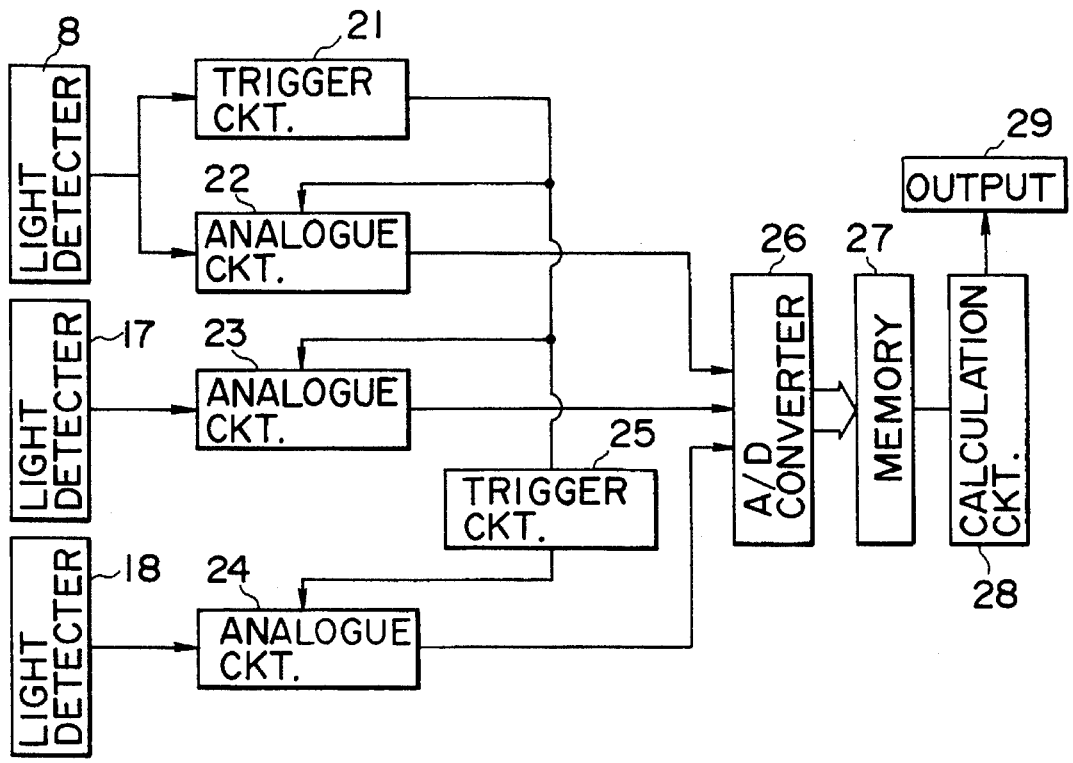
FIG. 3 is a block diagram of the signal processing unit of the apparatus according to the first embodiment.

The signals of the photodetectors 8, 17 and 18 are processed by a signal processing circuit as shown in FIG. 3. The forwardly scattered light output of the photodetector 8 is input as a pulse-like electrical signal to a trigger circuit 21 and an analogue processing circuit 22. The sideways scattered light output of the photodetector 17 and the fluorescence light output of the photodetector 18 are input to analogue processing circuits 23 and 24, respectively. In the analogue processing circuits 22, 23 and 24, the peak values and integrated values of the signal pulses are detected. When the particles come to the light applying position and the forwardly scattered light signal input to the trigger circuit 21 exceeds a predetermined level, a trigger signal is produced in response thereto for a predetermined period, and that signal is input to the analogue processing circuits 22 and 23. Each analogue processing circuit has the sampling and holding function so that the input signal may be processed only for the period during which a trigger signal is produced. Also, the trigger signal from the trigger circuit 21 is input to a trigger generating circuit 25 for fluorescence light, and this trigger generating circuit 25 for fluorescence light generates a trigger signal for a time $t_1$ to a time $t_2$, and that signal is input to the analogue processing circuit 24. Thereby, the signal of the photodetector 18 for fluorescence light can be sampled for the time $t_1$ to the time $t_2$ after the particle has passed through the light applying position 4. The outputs of the analogue processing circuits 22, 23 and 24 are converted into digital values by an A/D converting circuit 26, and are stored into a memory 27 as a forwardly scattered light signal, a sideways scattered light signal and a fluorescence light signal, respectively. On the basis of measurement parameters thus obtained regarding a number of specimens and memorized by the memory 27, the calculation of specimen analysis is effected in a calculation circuit 28, and the result of the calculation is output to an output unit 29 such as a CRT or a printer.

Figure 4:
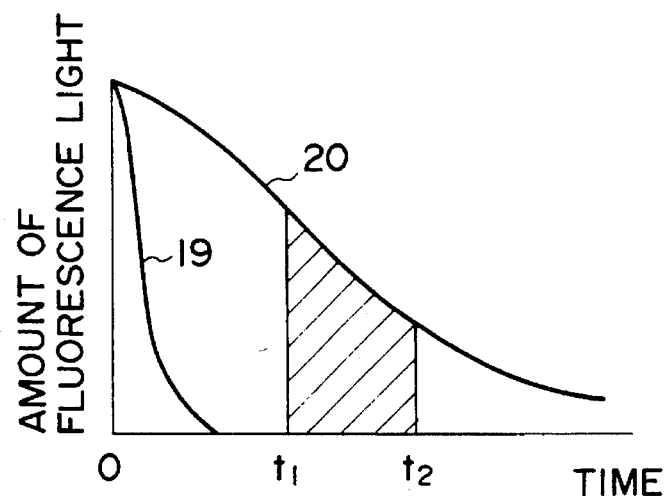
FIG. 4 is a graph of the life curve of fluorescence light.

The measurement principle of the present embodiment will now be described with reference to FIG. 4. The fluorescence dye used here is one whose fluorescence life is longer than that of ordinary self-fluorescence light or the like. FIG. 4 shows a graph of the life curve of fluorescence light excited by light application. The abscissa represents lapse time, and the moment at which light is applied to the particles in the examined portion and the application of the light has been finished is a time 0. The ordinate represents the intensity of fluorescence light created. In FIG. 4, curve 19 indicates the life curve by usually used fluorescence dye or self-fluorescence light possessed by cells or dust, and the life of fluorescence light from after it is excited until fluorescence light generation intensity becomes zero is about 100 nsec. In contrast, curve 20 is the life curve of the fluorescence dye having a longer life than usual which is used in the present embodiment, as for example, $Eu^{3+}$ chelate substance which has been used as the fluorescence dye. The life of fluorescence light in this case is 1000 nsec. or longer. This fluorescence light life curve has its peak output determined in conformity with the quantity of the fluorescence light coloring matter if the intensity of the laser light which excites fluorescence light is constant.

Figure 5:
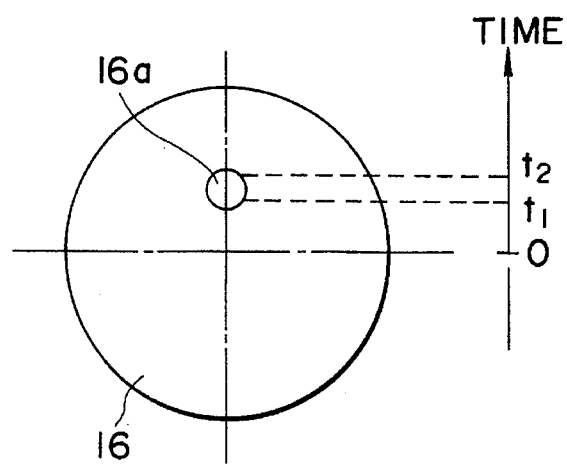
FIG. 5 shows the relation between the shape of an aperture and measurement time.

Assuming that light has been applied to the particles at the time 0, the creation of scattered lights ends in a moment, and the created amount of ordinary fluorescence light having a short fluorescence life or self-fluorescence light emitted by cells or dust becomes zero by the time $t_1$. The opening portion 16a of the aperture 16 shown in FIG. 5 is disposed conjugately with the non-applying position somewhat downstream of the light applying position to which a light spot is applied so that only the light from this portion may be directed to the photodetector 18. In other words, considering that the flow speed of the particles is constant, only the light in the hatched portion from the time $t_1$ to the time $t_2$ of FIG. 4 is metered. As is apparent from FIG. 4, only the fluorescence light of $Eu^{3+}$ chelate substance having a long fluorescence life is created during the time $t_1$ to $t_2$ and therefore, the intensity of genuinely desired fluorescence light can be measured without being affected by the mixing of the self-fluorescence light which is the other miscellaneous light than the desired fluorescence light or the light from other fluorescence dyes or the scattered lights.

The intensity of fluorescence light metered during the time $t_1$ to $t_2$ is a partial one which does not include the peak value, but this poses no problem because there is obtained a value substantially proportional to the peak output conforming to the quantity of the fluorescence dye. If necessary, a correction coefficient can be provided to the light metering output on the basis of the shape of this curve and the times $t_1$ and $t_2$ to thereby estimate the peak value or the integrated value. In this case, the measured value once memorized in the memory 27 is later corrected by a calculation process to thereby estimate the peak value or the integrated value.

Now, as a more specific example of the use of the above-described apparatus, a description will be made below of a method of making a reagent for examining the surface antigen of blood corpuscle cells by using $Eu^{3+}$ chelate substance as a fluorescence dye having a long fluorescence life of a predetermined period or longer, and the procedure of measurement using this reagent.

$Eu^{3+}$ chelate has a property of being excited by a wavelength in the vicinity of 300 nm and creating fluorescence light of a wavelength in the vicinity of 610 nm for a long time. First a monoclonal antibody uniquely coupling to the desired surface antigen on the surface of a cell which is a specimen is prepared and is converted into a biotinylated monoclonal antibody, and the $Eu^{3+}$ chelate is labelled on streptoavidin, and biotin and streptoavidin are coupled together, whereby there can be obtained a monoclonal antibody reagent having the $Eu^{3+}$ chelate labelled thereon.

Then, this reagent is mixed with a blood sample diluted to a moderate concentration and is reacted with the latter for a predetermined time, thereby accomplishing cell dyeing. By measuring this reacted sample liquid by the above-described apparatus, qualitative or quantitative measurement of the surface antigen of the cell can be accomplished from the measured intensity of the fluorescence light of the $Eu^{3+}$ chelate obtained.

Second Embodiment

Figure 6:
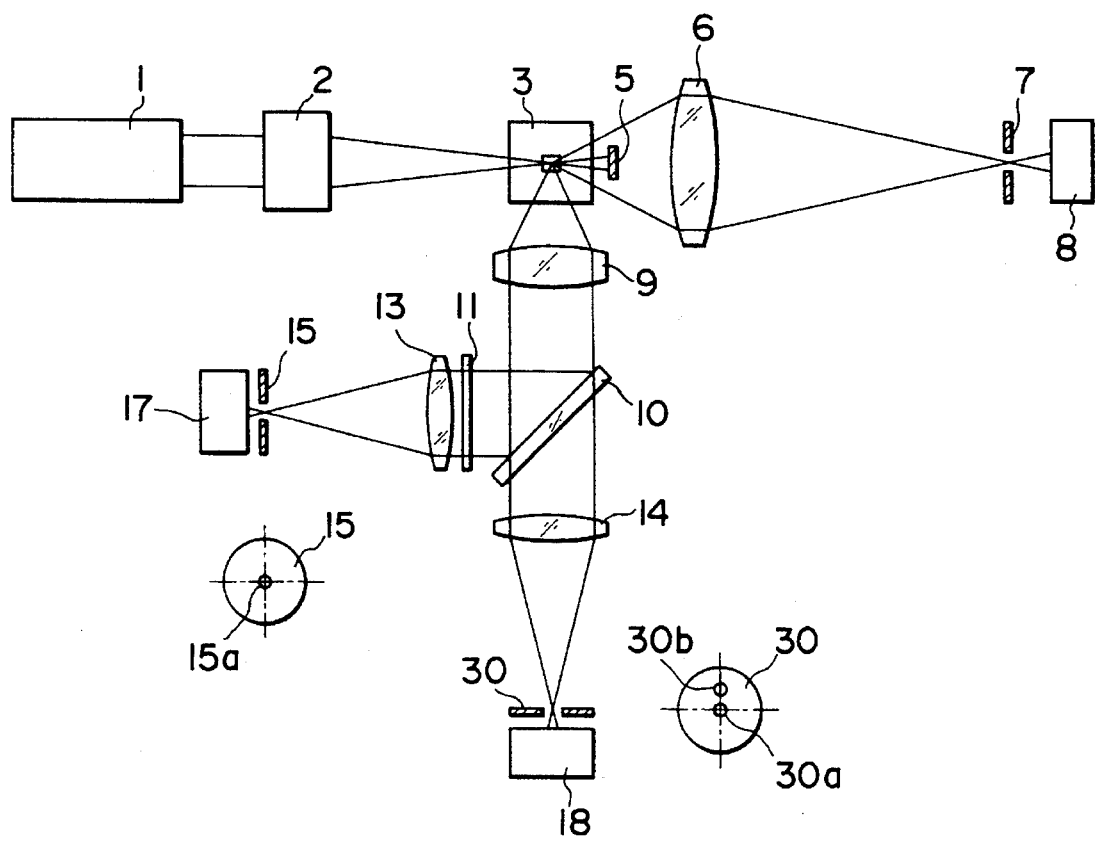
FIG. 6 shows the construction of an apparatus according to a second embodiment of the present invention.
Figure 7:
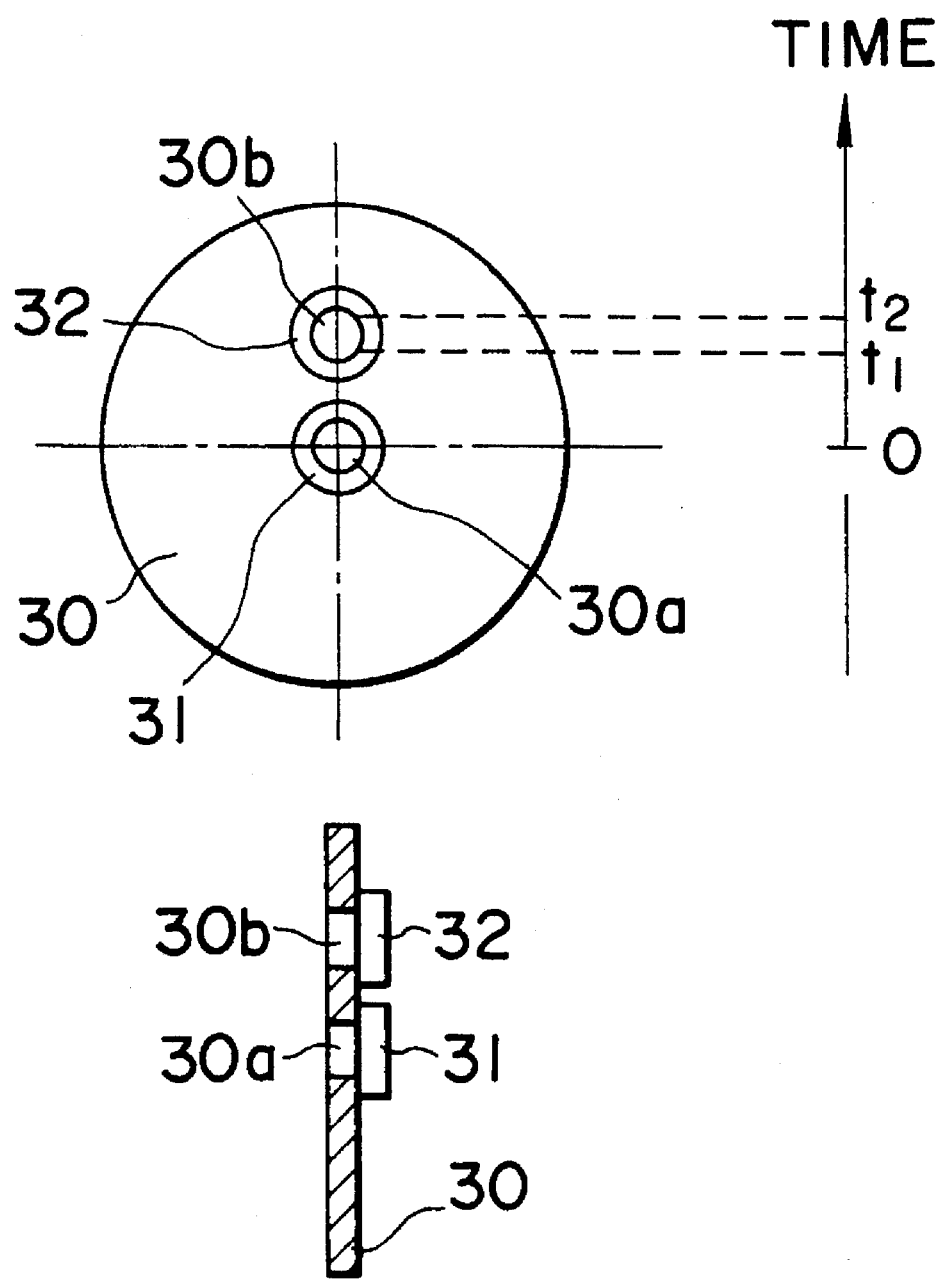
FIG. 7 shows the construction of an aperture in the second embodiment.

Description will now be made of a second embodiment of the present invention which can obtain more parameters. FIG. 6 shows the construction of the optical system of the second embodiment and corresponds to FIG. 2. In FIG. 6, reference characters identical to those in FIG. 2 designate identical or equivalent members. FIG. 7 shows the details of an aperture 30.

In the present embodiment, the band-pass filter 12 in FIG. 2 which shows the previous embodiment is omitted and an aperture 30 having a plurality of opening portions is disposed in place of the aperture 16. The detailed construction of the aperture 30 is as shown in FIG. 7. In FIG. 7, two opening portions 30a and 30b are provided at and near the central portion of the light-intercepting aperture 30. Band-pass filters 31 and 32 are attached to the opening portions 30a and 30b, respectively, and each of these band-pass filters has a property of selectively transmitting fluorescent light of a particular wavelength therethrough. The opening portion 30a is provided at the central portion of the aperture 30, and the opening portion 30b is provided somewhat above it. The opening portion 30a is conjugate with the light applying position 4, and the opening portion 30b is conjugate with a position somewhat downstream of the light applying position 4. That is, fluorescence light of a particular wavelength emitted from the light applying position 4 is selectively directed to the photodetector 18 by the opening portion 30a, and only fluorescence light of a particular wavelength from the non-applying position downstream of the light applying position 4 is directed to the photodetector 18 by the opening portion 30b. That is, design is made such that the light metering output pulses of two kinds of fluorescence lights are time-serially obtained in the photodetector 18, and two kinds of fluorescence light parameters are time-serially obtained in one and the same photodetector. In order to cope with more fluorescence dyes when using exciting plural kinds of fluorescence dyes at a time, a light source having a wide wavelength range such as a multi-oscillation laser source may be adopted or a plurality of light beams differing in wavelength from one another may be optically combined to thereby make a single light beam.

The measurement principle of the present embodiment will now be described with reference to FIG. 4. In the present embodiment, with a second fluorescence dye of a short fluorescence life usually used, a second fluorescence light whose fluorescence life is longer than ordinary self-fluorescence light or the like is selected. Alternatively, first and second fluorescence dyes both having a long fluorescence life are selected.

Where particles are dually dyed with two kinds of fluorescence dyes, i.e., the first fluorescence dye of the ordinary fluorescence life and the second fluorescence dye of a long fluorescence life such as $Eu^{3+}$ chelate, band-pass filters having the characteristics of selectively transmitting said first and second fluorescence lights therethrough are selected as the band-pass filters 31 and 32 of the aperture 30. In such a construction, each time a particle passes through the light applying position, the first and second fluorescence lights selectively and time-serially enter the photodetector 18, and two different fluorescence lights can be measured by a single photodetector. At this time, the second fluorescence light of a long light emission life is measured in the time range $t_1-t_2$ wherein the first fluorescence light is not created and therefore, very accurate measured values can be obtained without being subjected to the mixing of miscellaneous light.

It is also easy to further develop the construction of the above described embodiment. That is, if the number of openings in the aperture 30 is not limited to two, but a plurality of openings are provided conjugately with a plurality of non-applying positions along the flow of the particles, still more parameters can be obtained time-serially. In this case, plural kinds of fluorescence lights having a long fluorescence life are prepared and the particles are dyed with these at a time. Then, these fluorescence lights are wavelength-selected by band-pass filters formed on the respective opening portions and individually detected, whereby the intensities of the fluorescence lights of a plurality of parameters free of the influence of miscellaneous light can be obtained time-serially by one measurement.

Also, if the characteristic of the band-pass filter 31 is made such as to selectively transmit the wavelengths of scattered lights therethrough, the two different parameters of the sideways scattered light and fluorescent light can be obtained by one and the same photodetector 18. In this case, the scattered light and fluorescence light have a great intensity difference there been and therefore, it is preferable to use a photodetector 18 of a wide dynamic range or use a band-pass filter 31 having a high degree of light attenuation.

Thus, in the present embodiment, as in the previous embodiment, the intensity of fluorescence light measured by the utilization of the delay of time is entirely free of the influence of miscellaneous light and highly accurate and further, more kinds of measured parameters than the number of the photodetectors can be obtained, and this contributes to the compactness and reduced cost of the apparatus.

Now, as an example of the use of the apparatus of the present embodiment, description will be made below of a method of making a reagent for examining plural kinds of surface antigens on blood corpuscle cells at a time, and the procedure of the examination using this reagent.

Two kinds of first and second monoclonal antibodies uniquely coupling to first and second surface antigens, respectively, on the surface of a cell which is a specimen are first prepared. Further, two kinds of fluorescence dyes, i.e., a first fluorescence dye and a second fluorescence dye having a longer fluorescence life than the first fluorescence dye are prepared. The first fluorescence dye is then labelled on the first monoclonal antibody by a process similar to that previously described, and the second fluorescence dye is likewise labelled on the second monoclonal antibody. These are mixed together, whereby there can be obtained a reagent for examining two kinds of surface antigens at a time.

This reagent is then mixed with a blood sample diluted to moderate concentration and is reacted with the latter for a predetermined time, and each monoclonal antibody is coupled to a desired antigen on the surface of the cell, whereby the fluorescence dyeing of the cell is substantially effected through the monoclonal antibodies. This reacted sample liquid is measured by the above-described apparatus, and fluorescence lights of two colors are time-serially measured. When the first fluorescence light is detected, the presence of the first surface antigen can be confirmed, and when the second fluorescence light is detected, the presence of the second surface antigen can be confirmed. The quantity of the surface antigens can also be estimated from the intensity of the fluorescence lights. In this manner, the qualitative or quantitative measurements of two kinds of surface antigens can be accomplished at a time by one measurement.

We claim:

1. A specimen measuring method, comprising:

applying a light beam to a specimen dyed with a fluorescent dye;

detecting forward scattered light from the specimen within a period in which said light beam is applied;

setting a period in which said light beam is not applied after said detection of scattered light; and detecting at least one fluorescence light from said specimen within said period in which said light beam is not applied, whereby qualitative or quantitative measurements are provided for said specimen.

2. A method according to claim 1, wherein the specimen is dyed with said fluorescence dye by using an antibody attached to said fluorescence dye which uniquely couples to an antigen on the surface of the specimen.

3. A method according to claim 1, wherein said fluorescence dye comprises a Europium substance.

4. A method according to claim 1, wherein the specimen comprises a biological cell.

5. A specimen measuring method, comprising:

applying a light beam to a predetermined position;

passing a specimen dyed with a fluorescence dye through the predetermined position;

detecting forward scattered light from the specimen from the predetermined position within a period in which said light beam is applied;

setting a period of time in which said light beam is not applied after said detection of scattered light; and detecting at least one fluorescence light from said specimen at a position downstream of the light applying predetermined position within said period in which said light beam is not applied whereby qualitative or quantitative measurements are provided for said specimen.

6. A method according to claim 5, wherein said detection steps detect the light through an aperture by a photodetector.

7. A method according to claim 5, wherein the specimen is dyed with the fluorescence dye by using an antibody attached to said fluorescence dye which uniquely couples to an antigen on the surface of the specimen.

8. A method according to claim 5, wherein said fluorescence dye comprises a Europium substance.

9. A method according to claim 5, wherein the specimen comprises a biological cell.

10. A specimen measuring method, comprising:

applying a light beam to a specimen dyed with a first fluorescence dye and a second fluorescence dye and exciting said first and second fluorescence dyes at one time to generate first and second fluorescence lights, wherein, said first fluorescence dye and said second fluorescence dye have different fluorescence lifetimes;

time-serially detecting said first fluorescence light and said second fluorescence light from said specimen by using a single photodetector and two band-pass filters, whereby qualitative or quantitative measurements are provided for said specimen.

11. A method according to claim 10, further comprising:

detecting a scattered light from the specimen within an application period.

12. A method according to claim 10, wherein the specimen is dyed with the fluorescence dye by using an antibody attached to said fluorescence dye which uniquely couples to an antigen on the surface of the specimen.

13. A method according to claim 10, wherein said fluorescence dye comprises a Europium substance.

14. A method according to claim 10 wherein the specimen comprises a biological cell.

* * * * *